(12) United States Patent
Tomizawa et al.

(10) Patent No.: US 12,273,619 B2
(45) Date of Patent: Apr. 8, 2025

(54) IMAGE CAPTURING DEVICE, BIOLOGICAL INFORMATION ACQUISITION DEVICE, AND IMAGE CAPTURING METHOD

(71) Applicant: SHARP KABUSHIKI KAISHA, Sakai (JP)

(72) Inventors: Ryota Tomizawa, Sakai (JP); Hinatsu Ohgane, Sakai (JP); Tetsuya Okumura, Sakai (JP); Yoshihisa Adachi, Sakai (JP)

(73) Assignee: SHARP KABUSHIKI KAISHA, Sakai (JP)

(*) Notice: Subject to any disclaimer, the term of this patent is extended or adjusted under 35 U.S.C. 154(b) by 421 days.

(21) Appl. No.: 17/579,518

(22) Filed: Jan. 19, 2022

(65) Prior Publication Data

US 2022/0294985 A1    Sep. 15, 2022

(30) Foreign Application Priority Data

Mar. 9, 2021 (JP) .................................. 2021-037363

(51) Int. Cl.
*H04N 5/232* (2006.01)
*A61B 5/024* (2006.01)
*H04N 23/611* (2023.01)
*H04N 23/667* (2023.01)

(52) U.S. Cl.
CPC ....... *H04N 23/667* (2023.01); *A61B 5/02416* (2013.01); *H04N 23/611* (2023.01)

(58) Field of Classification Search
None
See application file for complete search history.

(56) References Cited

U.S. PATENT DOCUMENTS

| 8,326,571 | B2* | 12/2012 | Nagase ................... F24F 11/77 250/208.2 |
| 2006/0087561 | A1* | 4/2006 | Kojima .................. H04N 23/69 348/208.5 |
| 2009/0210193 | A1* | 8/2009 | Nagase ................... F24F 11/30 250/208.2 |
| 2012/0218517 | A1* | 8/2012 | Imamura .............. A61B 3/1025 382/128 |
| 2014/0063458 | A1* | 3/2014 | Imamura ................ G06V 40/19 382/134 |
| 2015/0065896 | A1* | 3/2015 | Takahashi ............ A61B 5/7207 600/500 |

(Continued)

FOREIGN PATENT DOCUMENTS

CN  110013102 A  7/2019
JP  2016-220915 A  12/2016

(Continued)

*Primary Examiner* — Mohammad J Rahman
(74) *Attorney, Agent, or Firm* — ScienBiziP, P.C.

(57) ABSTRACT

An image capturing device includes: an image capturing unit configured to capture a 4K or higher resolution moving image; and a selector switch configured to switch an image capturing mode in which the image capturing unit captures the moving image from a first image capturing mode to a second image capturing mode, the second image capturing mode providing a higher resolution in detecting an amount of change in pulse wave information representing a pulse wave of a living body in the captured moving image than does the first image capturing mode.

8 Claims, 11 Drawing Sheets

(56) References Cited

U.S. PATENT DOCUMENTS

| | | | | |
|---|---|---|---|---|
| 2016/0309997 | A1* | 10/2016 | Imamura | A61B 3/14 |
| 2017/0007113 | A1* | 1/2017 | Imamura | A61B 3/1025 |
| 2019/0197223 | A1 | 6/2019 | Otsuka et al. | |
| 2019/0217002 | A1* | 7/2019 | Urakabe | A61M 1/3639 |
| 2020/0175719 | A1* | 6/2020 | Wright | G06T 5/20 |
| 2020/0258208 | A1* | 8/2020 | Lota | G06N 20/00 |
| 2021/0051268 | A1* | 2/2021 | Chang | H04N 23/45 |
| 2021/0068670 | A1* | 3/2021 | Redtel | G06T 7/90 |
| 2021/0248389 | A1* | 8/2021 | Liu | H04N 7/188 |
| 2021/0366078 | A1 | 11/2021 | Tezuka et al. | |
| 2022/0012922 | A1* | 1/2022 | Ishikawa | G06F 3/013 |
| 2024/0062580 | A1* | 2/2024 | Li | G01S 5/18 |

FOREIGN PATENT DOCUMENTS

| | | |
|---|---|---|
| JP | 2019017876 A | 2/2019 |
| JP | 2020127169 A | 8/2020 |

* cited by examiner

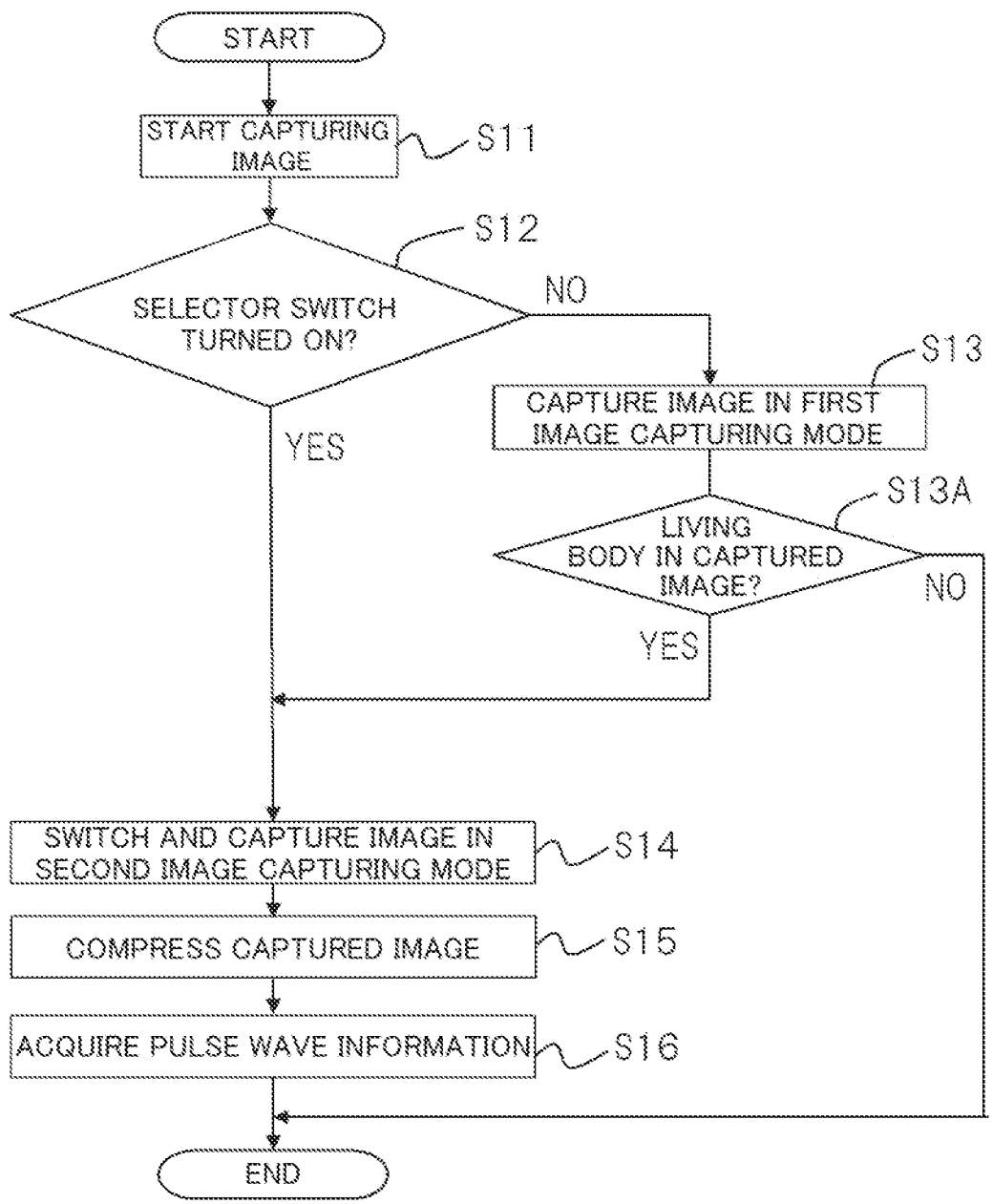

IMAGE CAPTURING DEVICE, BIOLOGICAL INFORMATION ACQUISITION DEVICE, AND IMAGE CAPTURING METHOD

CROSS-REFERENCE TO RELATED APPLICATION

The present application claims priority from Japanese Application JP2021-037363, the content of which is hereby incorporated by reference into this application.

The present disclosure, in an aspect thereof, relates to image capturing devices, biological information acquisition devices, and image capturing methods.

Japanese Unexamined Patent Application Publication, Tokukai, No. 2016-220915 discloses a pulse wave detection device for detecting a pulse wave from a captured image. This pulse wave detection device disclosed in Japanese Unexamined Patent Application Publication, Tokukai, No. 2016-220915 regulates the amount of light coming into a camera by adjusting the diaphragm of the camera on the basis of a pixel luminance value histogram prepared from a captured image in such a manner that the proportion of the pixels that have a luminance value lower than a prescribed value is greater than or equal to a threshold value. Japanese Unexamined Patent Application Publication, Tokukai, No. 2016-220915 describes that this particular structure can improve luminance even when there is an insufficient amount of light coming into the camera to capture an image.

SUMMARY OF THE INVENTION

There has been a demand for a simple and convenient process of switching camera settings to those that are suitable for detecting a pulse wave. The present disclosure, in an aspect thereof, has an object to provide an image capturing device, a biological information acquisition device, and an image capturing method, all of which provide a simple and convenient process of switching the image capturing mode to settings that are suitable for acquiring pulse wave information.

The present disclosure, in an aspect thereof, is directed to an image capturing device including: an image capturing unit configured to capture a 4K or higher resolution moving image; and a selector switch configured to switch an image capturing mode in which the image capturing unit captures the moving image from a first image capturing mode to a second image capturing mode, the second image capturing mode providing a higher resolution in detecting an amount of change in pulse wave information representing a pulse wave of a living body in the captured moving image than does the first image capturing mode.

The present disclosure, in another aspect thereof, is directed to an image capturing method including: acquiring an input signal; and switching an image capturing mode in which an image capturing unit captures a moving image from a first image capturing mode to a second image capturing mode in response to the acquisition of the input signal, the second image capturing mode providing a higher resolution in detecting an amount of change in pulse wave information representing a pulse wave of a living body in the captured moving image than does the first image capturing mode.

BRIEF DESCRIPTION OF THE DRAWINGS

FIG. 14 is a flow chart representing an exemplary operation of a control unit in accordance with Variation Example 1 of an embodiment.

DETAILED DESCRIPTION OF THE INVENTION

Embodiments

Figure 1:
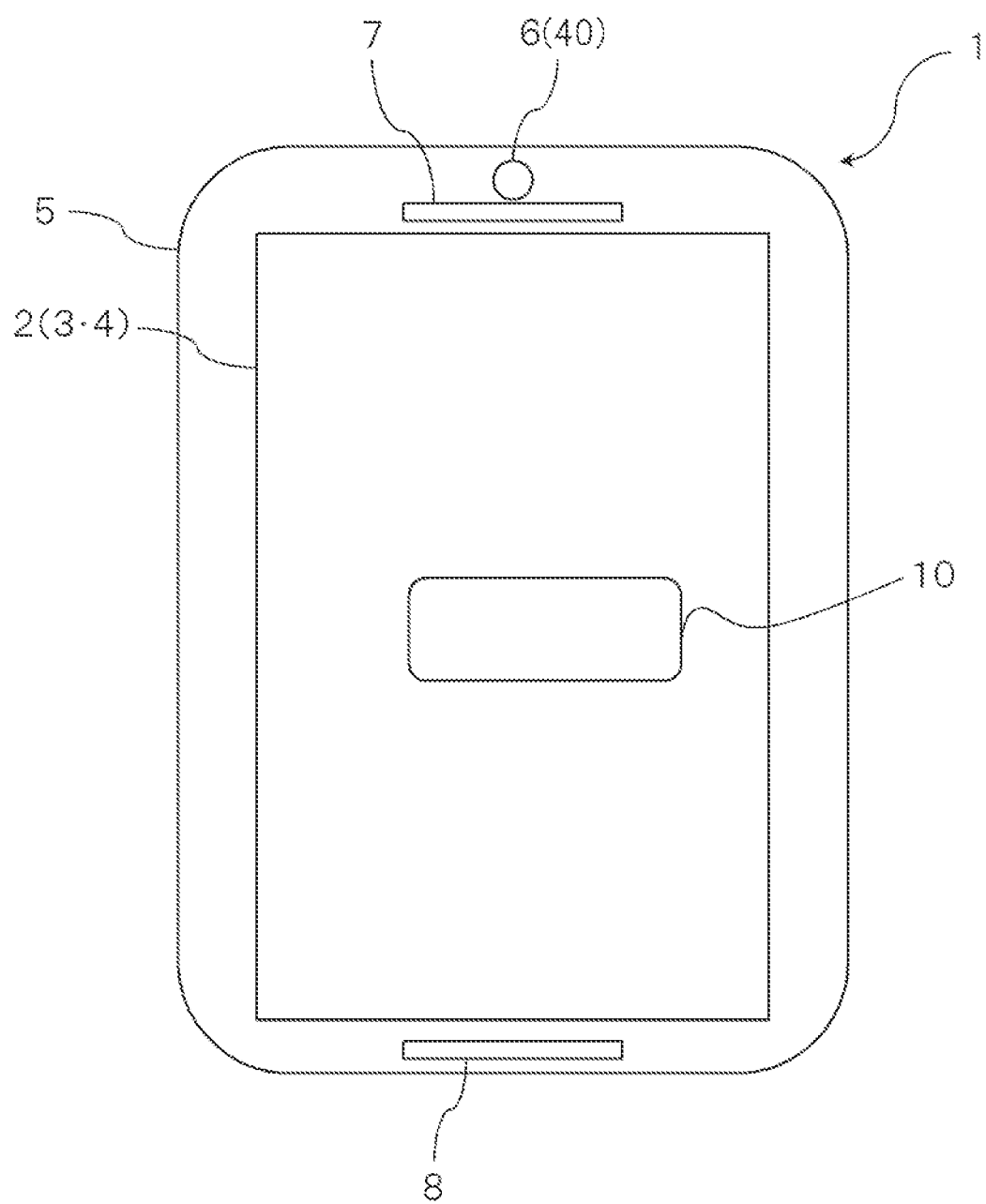
FIG. 1 is a front view of a mobile terminal in accordance with Embodiment 1.

The following will describe embodiments of the present disclosure with reference to drawings. Identical and equivalent elements in the drawings are denoted by the same reference numerals, and description thereof is not repeated.

FIG. 1 is a front view of a structure of a mobile terminal (biological information acquisition device) 1 in accordance with an embodiment. In other words, FIG. 1 illustrates the mobile terminal 1 in a plan view. The mobile terminal 1 is an example of a biological information acquisition device capable of acquiring pulse wave information representing the pulse wave of a human or other living body in a contactless manner.

For instance, the mobile terminal 1 includes an image capturing device 40 capable of capturing a moving image or plurality of successive still images of the body surface of a living body. When the moving image or plurality of successive still images captured on the image capturing device 40 shows the body surface of a living body, the mobile terminal 1 acquires pulse wave information representing the pulse wave of the living body in the captured image(s). For instance, the moving image or plurality of successive still images of the body surface shows changes in color of the body surface from one frame to the next (or from one still image to the next) due to the blood flow in the subject. The mobile terminal 1 can hence acquire pulse wave information for the subject from the changes in color of the body surface from one frame to the next (or from one still image to the next).

The description of the present embodiment assumes that, as an example, the mobile terminal 1 is a smartphone. For instance, the mobile terminal 1 approximately has such a size and weight that the mobile terminal 1 is portable. The mobile terminal 1 approximately has, for example, such a size that the user can hold the mobile terminal 1 in his/her hand. The mobile terminal 1 is not necessarily a smartphone and may be, for example, a tablet computer, a laptop computer, a digital camera, or any other electronic apparatus capable of capturing a moving image or plurality of successive still images.

The mobile terminal 1 includes, for example, a touch panel unit 2, a housing 5, an image capturing device 40, a speaker 7, and a microphone 8. The image capturing device 40 includes an image capturing unit 6. For instance, in the mobile terminal 1, the touch panel unit 2, the image capturing device 40 (including the image capturing unit 6), the speaker 7, and the microphone 8 are all provided, for example, in the same housing 5.

The touch panel unit 2 is an input device on which the user, or the subject, can make various inputs, as well as is a display device for displaying moving and still images. The touch panel unit 2 includes a display unit 3 and an input unit 4 disposed overlapping the display unit 3.

The display unit 3 is for displaying, for example, moving and still images. The display unit 3 has a display area for displaying, for example, moving and still images. The display unit 3 may be a liquid crystal display, an OLED (organic light-emitting diode) display, or any other display device capable of displaying, for example, moving and still images.

For instance, the display area of the display unit 3 (in other words, the display area of the touch panel unit 2) displays an image of a selector switch 10. The selector switch 10 is for switching the image capturing mode of the image capturing device 40 from a first image capturing mode to a second image capturing mode. The first image capturing mode is a default image capturing mode in which high-quality images are taken. The second image capturing mode is an image capturing mode in which images can be taken that are suitable for acquiring a pulse wave. The provision of the selector switch 10 enables the user to switch the image capturing mode of the image capturing device 40 from the first image capturing mode to the second image capturing mode by simply turning on the selector switch 10. The image capturing device 40 hence provides a simple and convenient process of switching the image capturing mode to settings that are suitable for acquiring pulse wave information.

The description of the present embodiment assumes that the selector switch 10 is an on screen button displayed as an image in the display area of the touch panel unit 2. The selector switch 10, which is an on screen button, receives a contact thereon of, for example, a finger or a touch pen as an input for output of an input signal. The selector switch 10 is not necessarily an on screen button and may be, for example, a hardware button with a hardware structure provided, for example, outside the display area of the touch panel unit 2 (e.g., on the housing 5). When the selector switch 10 is a hardware button, the selector switch 10 receives, for example, a tap or swipe as an input for output of an input signal.

The input unit 4 receives a contact thereon of, for example, a finger or a touch pen as a user input and generates an input signal for output based on the received input. The input unit 4 is, for example, a transparent touch sensor and disposed overlapping the display area of the display unit 3. Specifically, for example, the display unit 3 and the input unit 4 are integrated to form the touch panel unit 2. The input unit 4 is not necessarily a touch sensor and may be, for example, a hardware switch that receives a tap made by the user as ae user input.

The speaker 7 is a sound output device for generating sound from a sound signal. The microphone 8 is a sound input device for receiving, for example, sound external to the mobile terminal 1 such as a user's voice as an input and converting that sound to a sound signal.

The image capturing device 40 is an RGB camera capable of capturing a moving image or plurality of successive still images of the body surface of a subject from which pulse wave information is to be acquired. The image capturing device 40 captures a moving image at, for example, a prescribed frame rate (e.g., 10 to 300 fps (frame per second)) or captures a plurality of successive still images at prescribed image capturing intervals. The image capturing device 40 is, for example, an RGB camera with color channels for acquiring R (red), G (green), and B (blue) luminance values (alternatively referred to as "pixel values") respectively.

The image capturing device 40 is preferably a camera capable of capturing a moving image or plurality of successive still images with a 4K (2,160 pixels×3,840 pixels=8,294,400 pixels) or higher resolution. The image capturing device 40 may be, for example, a camera capable of capturing a moving image with a DCI 4K (2,160 pixels×4,096 pixels=8,847,360 pixels) resolution. The image capturing device 40 may be, for example, a camera capable of capturing a moving image or plurality of successive still images with an 8K (4,320 pixels×7,680 pixels=33,177,600 pixels) resolution. The image capturing device 40 may be, for example, a camera capable of capturing a moving image or plurality of successive still images with a lower-than-4K resolution such as the full high vision resolution (1,920 pixels×1,080 pixels=2,073,600 pixels).

The image capturing device 40 does not necessarily acquire the RGB colors and may acquire non-RGB colors such as cyan, magenta, and orange. The image capturing device 40 does not necessarily acquire a luminance value from visible light and may acquire a luminance value from invisible light such as infrared light. Also, the image capturing device 40 does not necessarily have three color channels and may have a single channel.

The image capturing unit 6 is a part of the image capturing device 40 that constitutes a sensor device including a light-receiving unit of the camera. The light-receiving unit in the image capturing unit 6 is covered by a transparent cover exposed outside the mobile terminal 1. The transparent cover covering the light-receiving unit in the image capturing unit 6 may be exposed on the front face of the mobile terminal 1 (the side on which an image is displayed on the touch panel unit 2) or on the rear face of the mobile terminal 1 (the opposite side from the front face).

For instance, the image capturing unit 6 may be a CMOS (complementary MOS) sensor device. The image capturing unit 6 is preferably a sensor device with at least 4K pixels (2,160 pixels×3,840 pixels=8,294,400 pixels). For instance, the image capturing unit 6 may be a DCI 4K sensor device with 2,160 pixels×4,096 pixels=8,847,360 pixels. For instance, the image capturing unit 6 may be an 8K sensor device with 4,320 pixels×7,680 pixels=33,177,600 pixels. The image capturing unit 6 may be, for example, any sensor device with fewer than 4K pixels such as a full high vision sensor device with 1,920 pixels×1,080 pixels=2,073,600 pixels.

Figure 2:
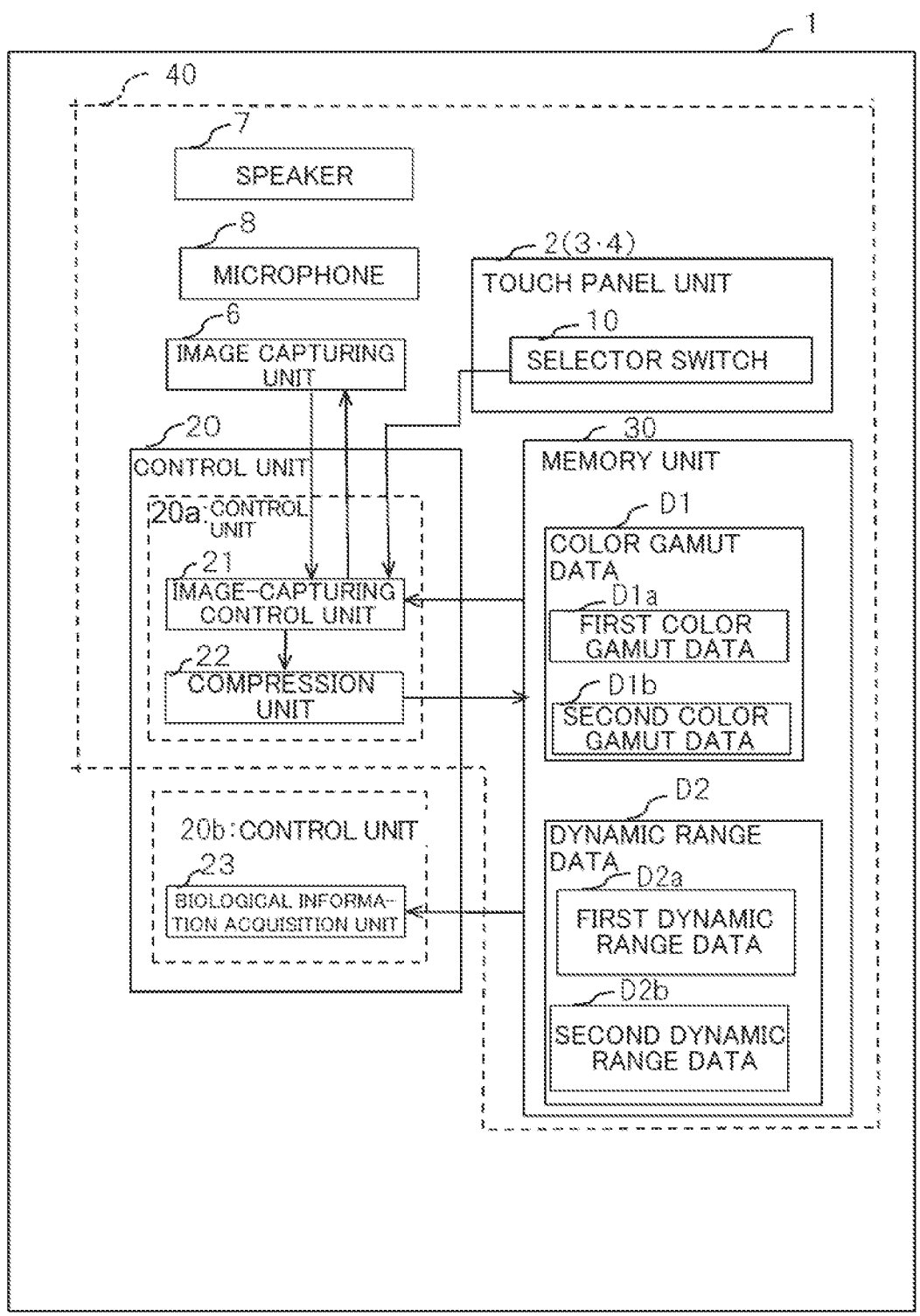
FIG. 2 is a functional block diagram of the mobile terminal in accordance with Embodiment 1.

FIG. 2 is a functional block diagram of the mobile terminal 1 in accordance with an embodiment. Referring to FIG. 2, the mobile terminal 1 includes a control unit 20 and a memory unit 30 as well as the touch panel unit 2, the image capturing unit 6, the speaker 7, the microphone 8, and the selector switch 10. The control unit 20 includes, for example, an image-capturing control unit 21, a compression unit 22, and a biological information acquisition unit 23. The compression unit 22 may be omitted when the moving image or plurality of successive still images generated by the image-capturing control unit 21 is not compressed.

The image capturing device 40 includes: the touch panel unit 2; the image capturing unit 6; the speaker 7; the microphone 8; the selector switch 10; the memory unit 30; and a control unit 20a including the image-capturing control unit 21 and the compression unit 22.

As an example, an information acquisition device in accordance with the present embodiment may alternatively include the image capturing device 40 and an information terminal including: a control unit 20b including the biological information acquisition unit 23; and a memory unit (not shown), in which case, the image capturing device 40 may be an independent apparatus, and the information terminal may be an independent apparatus separate from the image capturing device 40. The information terminal is, for example, a personal computer.

The control unit 20 includes, for example, a processor such as a CPU (central processing unit), to collectively control various functions of the mobile terminal 1. When the control unit 20 includes the control unit 20a and the control unit 20b, each of the control unit 20a and the control unit 20b includes, for example, a processor such as a CPU.

The memory unit 30 may be built around, for example, a hard disk, a SSD (solid state drive), or a semiconductor memory. The memory unit 30 may be a recording medium fixedly provided inside the mobile terminal 1 as a part of the mobile terminal 1 or may be a recording medium removable from the mobile terminal 1 such as an SIM card. The memory unit 30 contains, for example, various parametric data, an image-capturing program, and an information acquisition program, all either preinstalled or installed from a server communicable with the mobile terminal 1 for use in generating images such as a moving image or plurality of successive still images. This various parametric data may be, for example, color gamut data D1 or dynamic range data D2.

The color gamut data D1 is for specifying a color gamut for an image to be generated and includes first color gamut data D1a that is relatively broad and second color gamut data D1b that is relatively narrow compared to the first color gamut data D1a. The dynamic range data D2 is for specifying a dynamic range for an image to be generated and includes first dynamic range data D2a that is relatively broad and second dynamic range data D2b that is relatively narrow compared to the first dynamic range data D2a.

The image-capturing program causes the control unit 20 (computer) to function as the image-capturing control unit 21 and the compression unit 22. The information acquisition program causes the control unit 20 (computer) to function as the biological information acquisition unit 23.

The image-capturing control unit 21 operates in conjunction with the image capturing unit 6 to capture a moving image or plurality of successive still images. For instance, the image-capturing control unit 21, upon acquiring an input signal from the input unit 4, outputs a drive signal to the image capturing unit 6 on the basis of the input signal to drive the image capturing unit 6. Then, the image-capturing control unit 21, upon acquiring an electric signal produced by the image capturing unit 6 through photoelectric conversion, generates a moving image or plurality of successive still images (image) on the basis of the various parametric data stored in the memory unit 30.

The image-capturing control unit 21 switches the image capturing mode between the first image capturing mode and the second image capturing mode in response to an input signal from the input unit 4, to capture a moving image or plurality of successive still images using the image capturing unit 6.

The first image capturing mode is for capturing a relatively high quality moving image or plurality of successive still images compared to the second image capturing mode. The second image capturing mode is for capturing a moving image or plurality of successive still images that provides a relatively high resolution compared to the first image capturing mode in detecting the amount of change in pulse wave information representing the pulse wave of a living body captured in the moving image or plurality of successive still images.

In other words, the first image capturing mode is for capturing moving or still images for general purposes, not necessarily for specific purposes of acquiring pulse wave information for a living body. The second image capturing mode is for capturing a moving image or plurality of successive still images from which pulse wave information for a living body can be acquired with high precision.

Specifically, when the image-capturing control unit 21 acquires an image-capturing command signal (input signal from the input unit 4) instructing for a start of capturing a moving image or plurality of successive still images, but acquires no switching signal (input signal) indicating that the selector switch 10 has been turned on, the image-capturing control unit 21 starts capturing such an image or images in the first image capturing mode. In the first image capturing mode, for example, the image-capturing control unit 21 controls to drive the image capturing unit 6 upon acquiring an image-capturing command signal. Then, the image-capturing control unit 21, upon acquiring an electric signal produced by the image capturing unit 6 through photoelectric conversion, accesses the memory unit 30, selects the first color gamut data D1a and the first dynamic range data D2a respectively from the first color gamut data D1a and the second color gamut data D1b and from the first dynamic range data D2a and the second dynamic range data D2b for the generation of a moving image or plurality of successive still images with higher image quality in the color gamut data D1 and in the dynamic range data D2, and generates such an image or images.

Meanwhile, when the image-capturing control unit 21 acquires an image-capturing command signal (input signal from the input unit 4) instructing for a start of capturing a moving image or plurality of successive still images and acquires a switching signal (input signal) indicating that the selector switch 10 has been turned on, the image-capturing control unit 21 switches from the first image capturing mode to the second image capturing mode and starts capturing such an image or images in the second image capturing mode. In the second image capturing mode, for example, the image-capturing control unit 21 controls to drive the image capturing unit 6 upon acquiring an image-capturing command signal and a switching signal. Then, the image-capturing control unit 21, upon acquiring an electric signal produced by the image capturing unit 6 through photoelectric conversion, accesses the memory unit 30, selects the second color gamut data D1$b$ and the second dynamic range data D2$b$ respectively from the first color gamut data D1$a$ and the second color gamut data D1$b$ and from the first dynamic range data D2$a$ and the second dynamic range data D2$b$ for the generation of a moving image or plurality of successive still images that provides a higher resolution in detecting the amount of change in pulse wave information representing the pulse wave of a living body in the color gamut data D1 and in the dynamic range data D2, and generates such an image or images.

In other words, the image-capturing control unit 21 generates a moving image or still images with both the color gamut and the dynamic range being shrunk in input/output characteristics in the second image capturing mode compared to in the first image capturing mode. The "input/output characteristics" here refers to the relationship between the amount of light received by the image capturing unit 6 and the luminance values of the pixels in the image capturing unit 6.

Figure 3:
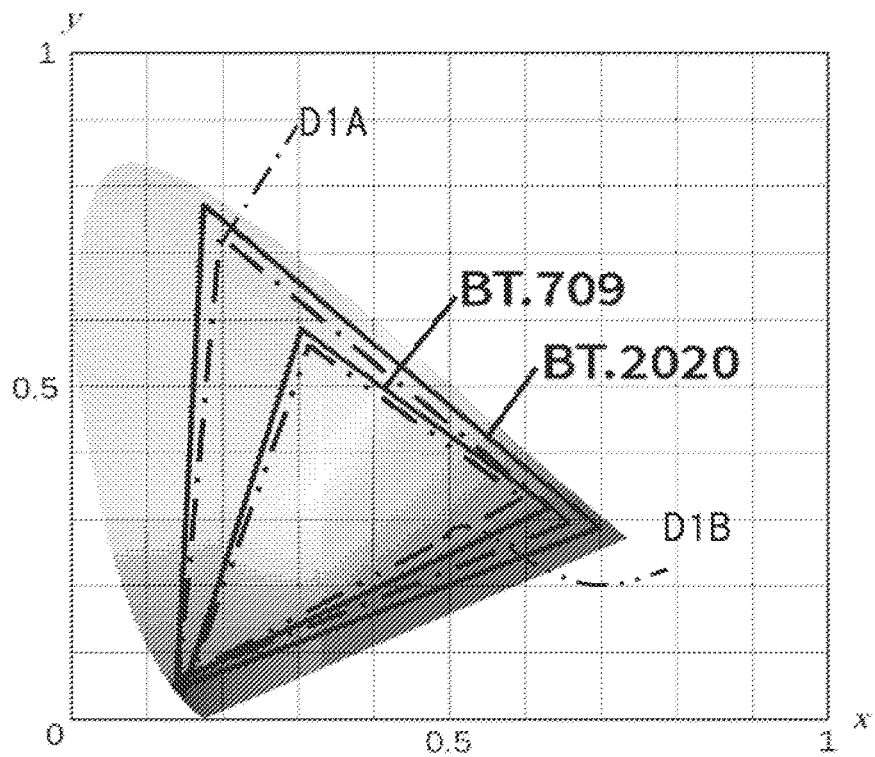
FIG. 3 is a diagram representing a first color gamut represented by first color gamut data and a second color gamut represented by second color gamut data, both the first color gamut data and the second color gamut data being stored in a memory unit in accordance with an embodiment.

FIG. 3 is a diagram representing a first color gamut D1A (indicated by a dash-dot line in FIG. 3) represented by the first color gamut data D1$a$ stored in the memory unit 30 in accordance with an embodiment and a second color gamut D1B (indicated by a dash-double-dot line in FIG. 3) represented by the second color gamut data D1$b$ stored in the memory unit 30 in accordance with an embodiment. In FIG. 3, color space coordinates, x and y, are used to represent the first color gamut D1A and the second color gamut D1B.

The first color gamut D1A is broader than the second color gamut D1B. For instance, the first color gamut D1A is so broad as to substantially cover BT. 2020 and is broader than BT. 709. The image-capturing control unit 21 can hence, in the first image capturing mode, generate a high-quality, vivid color moving image or still images reproduced using the first color gamut D1A with a broad color reproduction range, by, for example, generating a moving image or still images, using the first color gamut data D1$a$, from an electric signal produced through photoelectric conversion by the image capturing unit 6 including a 4K-equivalent number of pixels. The image-capturing control unit 21 can hence generate a higher quality moving image or still images in the first image capturing mode than in the second image capturing mode. The first color gamut D1A is not necessarily limited to the color gamut described above so long as the first color gamut D1A is broader than the second color gamut D1B.

The second color gamut D1B is narrower than the first color gamut D1A. For instance, the second color gamut D1B is as broad as BT. 709. In other words, the second color gamut D1B is shrunk for better representation of the color gamut for the color changes of the body surface when compared to the first color gamut D1A. The image-capturing control unit 21 can hence, in the second image capturing mode, generate a moving image or plurality of successive still images in the second color gamut D1B narrower than the first color gamut D1A and shrunk to the color gamut for the color changes of the body surface, by, for example, generating a moving image or plurality of successive still images, using the second color gamut data D1$b$, from an electric signal produced through photoelectric conversion by the image capturing unit 6 including a 4K-equivalent number of pixels.

The second color gamut D1B is not necessarily limited to the color gamut described above so long as the second color gamut D1B is narrower than the first color gamut D1A and shrunk to the color gamut for the color changes of the body surface.

As described here, the image-capturing control unit 21 obtains an electric signal from the image capturing unit 6 using the same high resolution pixels (e.g., a 4K-equivalent number of pixels) in the second image capturing mode as well as in the first image capturing mode.

The image-capturing control unit 21 then, in the second image capturing mode, generates a moving image or plurality of successive still images in the second color gamut D1B from an electric signal obtained from the image capturing unit 6. The second color gamut D1B is deliberately rendered narrower than the first color gamut D1A that is for use in the first image capturing mode and shrunk closer to the color gamut in which the body surface color (e.g., skin color) of a living body changes. In other words, the image-capturing control unit 21 generates a moving image or plurality of successive still images in which smaller changes in the body surface color of a living body are reproduced by using the second image capturing mode than by using the first image capturing mode.

Consequently, the image-capturing control unit 21 is capable of generating, in the second image capturing mode, a moving image or plurality of successive still images that provides a higher resolution in detecting the amount of change in pulse wave information representing a pulse wave from the moving image or plurality of successive still images when compared to a moving image or still images reproduced using the first color gamut DIA. This particular configuration enables the generation of a moving image or plurality of successive still images from which pulse wave information precisely representing the actual pulse wave can be acquired. The mobile terminal 1 can hence acquire pulse wave information precisely representing the pulse wave of a living body.

Figure 4:
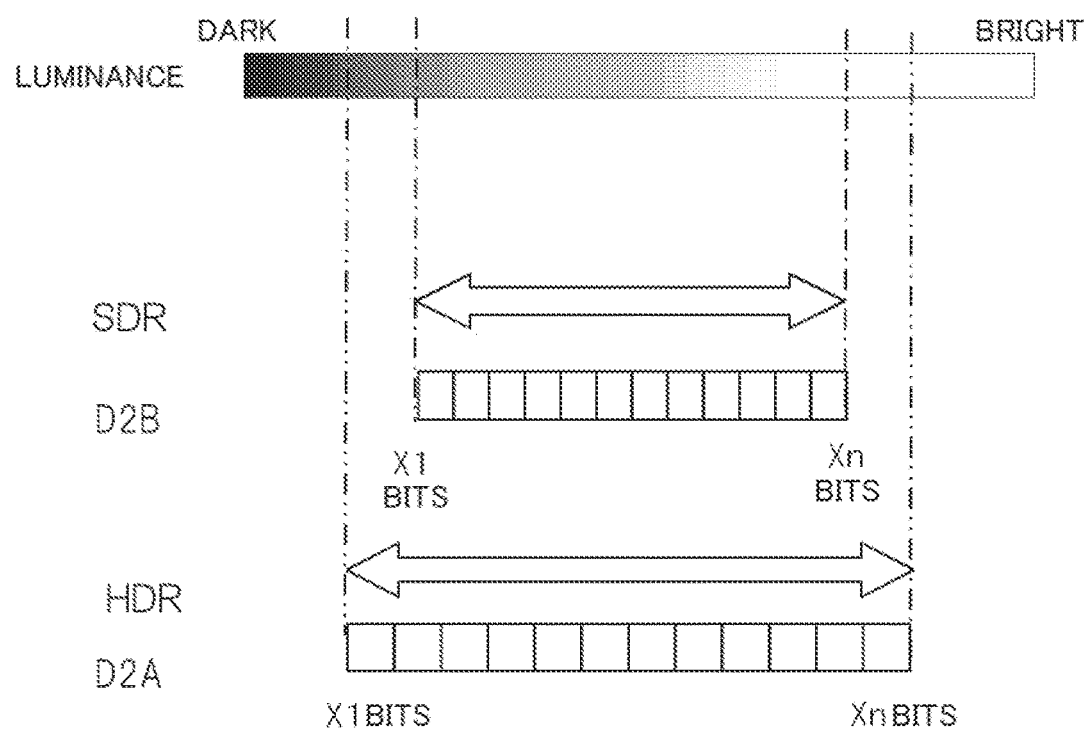
FIG. 4 is a diagram of a first dynamic range represented by first dynamic range data and a second dynamic range represented by second dynamic range data, both the first dynamic range data and the second dynamic range data being stored in a memory unit in accordance with an embodiment.

FIG. 4 is a diagram representing a first dynamic range D2A (denoted by D2A in FIG. 4) represented by the first dynamic range data D2$a$ stored in the memory unit 30 in accordance with an embodiment and a second dynamic range D2B (denoted by D2B in FIG. 4) represented by the second dynamic range data D2$b$ stored in the memory unit 30 in accordance with an embodiment. FIG. 4 shows the range of the luminance of light incident to the image capturing unit 6.

As described earlier, the first dynamic range D2A represented by the first dynamic range data D2$a$ is broader than the second dynamic range D2B represented by the second dynamic range data D2$b$.

The first dynamic range D2A is, as an example, an approximate equivalent of HDR (high dynamic range), and the second dynamic range D2B is, as an example, an approximate equivalent of SDR (standard dynamic range), which is narrower than HDR.

Then, for example, the image-capturing control unit 21 can, in the first image capturing mode, generate a moving image or still images in the first dynamic range D2A with a broad luminance range and natural brightness, by, for example, generating a moving image or still images, using the first dynamic range data D2a, from an electric signal produced through photoelectric conversion by the image capturing unit 6 including a 4K-equivalent number of pixels. The image-capturing control unit 21 can hence generate a higher quality moving image or still images with a broader dynamic range in the first image capturing mode than in the second image capturing mode.

The second dynamic range D2B is narrower than the first dynamic range D2A. In other words, the second dynamic range D2B provides a narrower range of luminance than the first dynamic range D2A, by using the same amount of data as the first dynamic range D2A. As an example, both the first dynamic range D2A and the second dynamic range D2B are represented by n bits (from the XI-th bit to the Xn-th bit). The second dynamic range D2B, despite using the same number of bits as the first dynamic range D2A, is deliberately specified to represent a narrower range of luminance than the first dynamic range D2A.

The image-capturing control unit 21, in the second image capturing mode, deliberately uses a narrower range of luminance than the range of luminance represented by the first dynamic range D2A used in the first image capturing mode as described here. The image-capturing control unit 21 hence generates a moving image or plurality of successive still images in which smaller changes in a narrower range of luminance are reproduced from an electric signal received from the image capturing unit 6 in the second image capturing mode than in the first image capturing mode. A moving image or plurality of successive still images in which even small changes in luminance are represented, as described here, shows even small changes in the color of a body surface (e.g., changes in the skin color) that shows a pulse wave, respectively, in the frames of the moving image or from one still image to the next.

As described here, the image-capturing control unit 21 is capable of, in the second image capturing mode, generating a moving image or plurality of successive still images that provides a higher resolution in detecting the amount of change in pulse wave information representing a pulse wave from the moving image or plurality of successive still images when compared to a moving image or still images reproduced using the first dynamic range D2A. This particular configuration enables the generation of a moving image or plurality of successive still images from which pulse wave information precisely representing the actual pulse wave can be acquired. The mobile terminal 1 can hence precisely acquire the actual pulse wave.

Meanwhile, particularly either when there is a small number of gray levels available to the image-capturing control unit 21 for representing pixel values in generating a moving image or plurality of still images or when the compression unit 22 compresses a moving image or plurality of successive still images, it is better to reduce, to a possible minimum, the range of luminance that is not required to acquire changes in the body surface color of a living body.

Therefore, either when there is a small number of gray levels available to the image-capturing control unit 21 for representing pixel values in generating a moving image or plurality of still images or when the compression unit 22 compresses a moving image or plurality of successive still images, the representation of a moving image or plurality of still images using a dynamic range that is narrower than the first dynamic range D2A such as the second dynamic range D2B is particularly highly effective in obtaining high precision pulse wave information.

Figure 5:
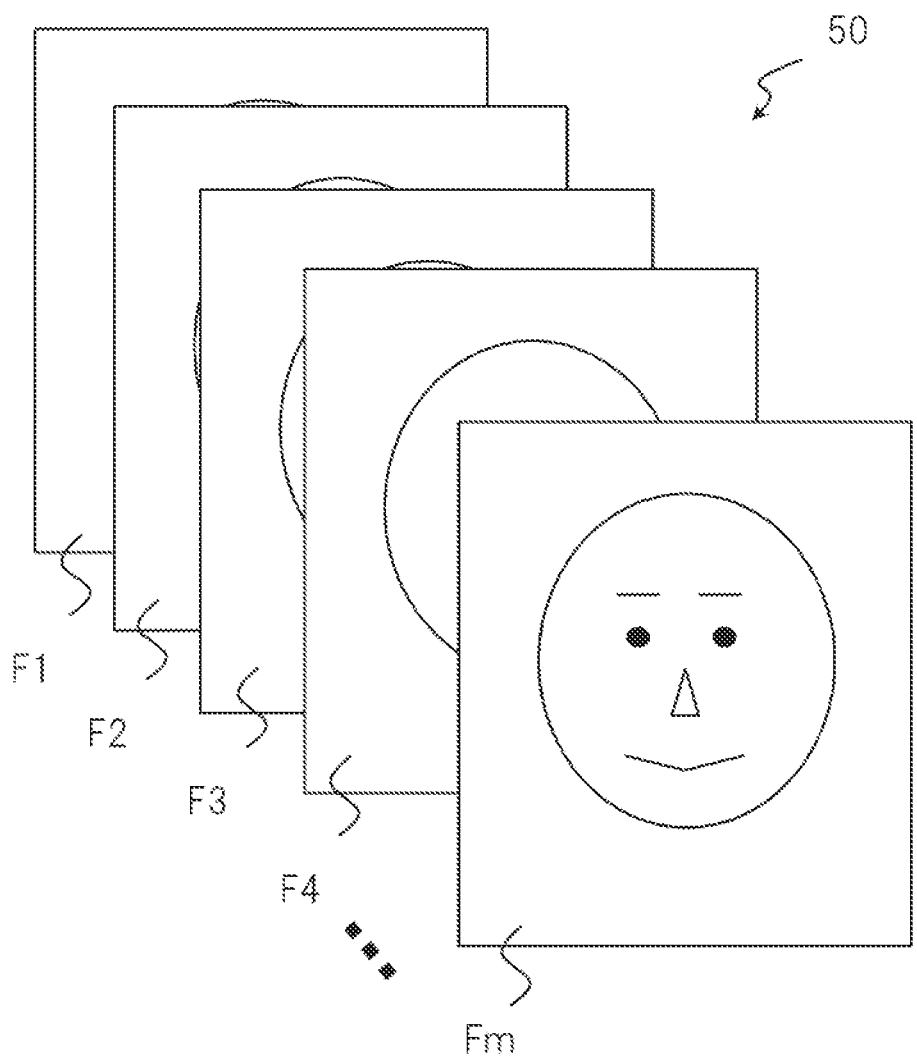
FIG. 5 is a schematic view of a moving image generated by an image-capturing control unit in accordance with an embodiment.

FIG. 5 is a schematic view of a moving image generated by the image-capturing control unit 21 in accordance with an embodiment. For instance, the image-capturing control unit 21 generates a moving image containing a plurality of successive frames, Frame F1, Frame F2, Frame F3, Frame F4, . . . , and Frame Fm.

The moving image or plurality of successive still images generated by the image-capturing control unit 21 may be stored in the memory unit 30, without being compressed, and subsequently sent to the biological information acquisition unit 23 for acquisition of pulse wave information. Alternatively, the moving image generated by the image-capturing control unit 21 may be compressed and stored in the memory unit 30 and subsequently decompressed and sent to the biological information acquisition unit 23 for acquisition of pulse wave information. The moving image generated by the image-capturing control unit 21 is preferably temporarily compressed for storage in the memory unit 30 because a high resolution moving image such as a 4K or 8K image contains a large amount of information.

In response to the image-capturing control unit 21 generating a moving image or plurality of successive still images, the compression unit 22 compresses the generated moving image or plurality of successive still images and stores the compressed image(s) in the memory unit 30. The compression unit 22 preferably compresses the image(s) by reversible compression, but may compress the image(s) by irreversible compression to further reduce the amount of information.

The bit rate is preferably greater than or equal to 200 Mbps when the image(s) subjected to compression is/are an 8K moving image and is greater than or equal to 50 Mbps when the image(s) subjected to compression is/are a 4K moving image.

The compression unit 22 preferably separately compresses either each Frame F1, F2, . . . , and Fm in the moving image captured by the image capturing unit 6 and the image-capturing control unit 21 or each of the plurality of successive still images captured by the image capturing unit 6 and the image-capturing control unit 21. In other words, to compress a moving image, the compression unit 22 preferably separately compresses each individual frame (e.g., compresses only Frame F1, only Frame F2, and so on) rather than collectively compresses multiple frames together. To compress a plurality of successive still images, the compression unit 22 preferably separately compresses each individual still image rather than collectively compresses a plurality of still images together.

This is because, as will be described later, the pulse wave information is acquired on the basis of changes in the body surface that are captured over multiple frames (or a plurality of still images), and more precise pulse wave information can be obtained by separately compressing each individual frame (each individual still image) than by collectively compressing multiple frames (or a plurality of still images) together.

The compression unit 22 has been described so far assuming that the compression unit 22 compresses a moving image or plurality of successive still images before the biological information acquisition unit 23 acquires pulse wave information from the image(s). Alternatively, the compression unit 22 may compress a moving image or plurality of successive still images at any suitable timing. As an example, the compression unit 22 may compress a moving image or plurality of successive still images and store the compressed image(s) in the memory unit 30, after the biological information acquisition unit 23 acquires the pulse wave information from the image(s). As another example, the compression unit 22 may compress a moving image or plurality of successive still images for storage in the memory unit 30 while the biological information acquisition unit 23 is acquiring pulse wave information from the image(s) (e.g., after the biological information acquisition unit 23 has detected a face and/or other features from the image(s)).

Figure 6:
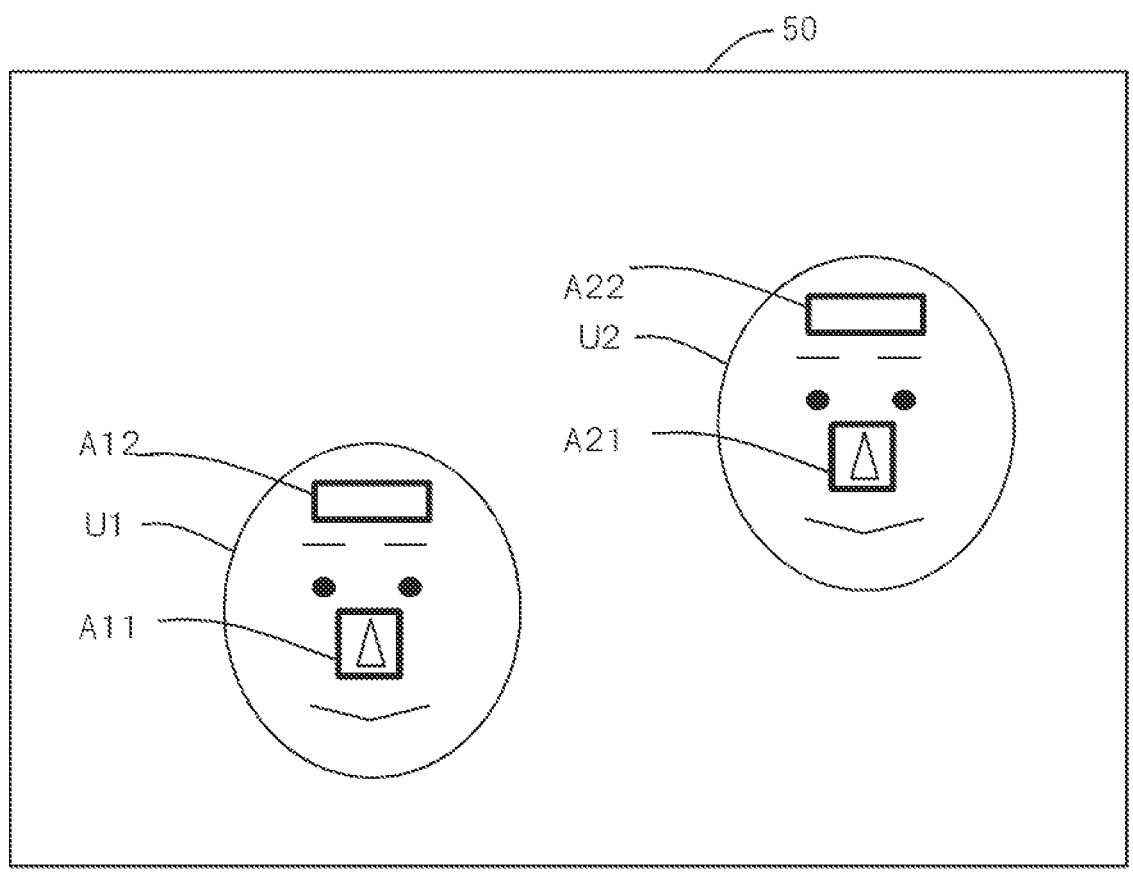
FIG. 6 is a drawing illustrating a situation where a biological information acquisition unit in accordance with an embodiment is acquiring pulse wave information representing a pulse wave from the image.

FIG. 6 is a drawing illustrating a situation where the biological information acquisition unit 23 in accordance with an embodiment is acquiring pulse wave information representing a pulse wave from an image 50.

The biological information acquisition unit 23 acquires pulse wave information representing a pulse wave by processing a moving image or plurality of successive still images retrieved from the memory unit 30. When the memory unit 30 contains a compressed moving image or plurality of successive still images, the biological information acquisition unit 23 acquires pulse wave information representing a pulse wave by processing the image(s) after decompressing the image(s). These moving and successive still images will be referred to as the image 50.

For instance, the biological information acquisition unit 23 identifies a part of the body surface of a living body captured in the image 50 (e.g., a part of, for example, the forehead, cheek, or jaw) and extracts changes in the body surface color of the living body that appear in that identified part from one frame to the next (or from one still image to the next). The biological information acquisition unit 23 then acquires pulse wave information representing a pulse wave from the extracted changes in the body surface color.

Assume, as an example, that the image 50 shows the faces of multiple people (two people) as in FIG. 6. The biological information acquisition unit 23 may acquire pulse wave information from one of the people or from every person in the image 50.

For instance, the biological information acquisition unit 23 identifies a predetermined feature (e.g., nose) of a first face U1 captured in the image 50 and then identifies, in the image 50, a region A11 containing the identified feature (e.g., nose). The biological information acquisition unit 23 then identifies, in the image 50, a target region A12 (e.g., forehead), separated by a prescribed distance from the region A11 containing the identified feature (e.g., nose), from which pulse wave information can be easily acquired. The target region A12 is not necessarily limited to the forehead and may be any region of the first face U1, for example, the whole face or the cheek.

As in the case of the first face U1, the biological information acquisition unit 23 identifies a predetermined feature (e.g., nose) of a second face U2 captured in the image 50 and then identifies, in the image 50, a region A21 containing the identified feature (e.g., nose). The biological information acquisition unit 23 then identifies, in the image 50, a target region A22 (e.g., forehead), separated by a prescribed distance from the region A21 containing the identified feature (e.g., nose), from which pulse wave information can be easily acquired.

The biological information acquisition unit 23 then acquires pulse wave information representing a pulse wave from changes in the body surface color in each of the target regions A12 and A22 from one frame to the next when the image 50 is a moving image and from changes in the body surface color in each of the target regions A12 and A22 from one still image to the next when the image 50 is a plurality of successive still images.

Specifically, for example, the biological information acquisition unit 23 calculates a representative value for the pixel values in the target region A12. This representative value may be, for example, a statistic quantity, such as an average, median, or most frequent value, for the pixel values of the pixels in the target region A12. The biological information acquisition unit 23 calculates a representative value for each color channel (e.g., each of R (red), G (green), and B (blue)) for the target region A12. The biological information acquisition unit 23 then calculates pulse wave information representing a pulse wave from the calculated representative value for each color channel by, for example, one of various feasible methods such as main component analysis, independent component analysis, and pigmentation component separation. The biological information acquisition unit 23 similarly calculates pulse wave information for the target region A22. This particular configuration enables the biological information acquisition unit 23 to acquire biological information from a moving image or plurality of successive still images.

The living body is not necessarily a human body and may be a living body other than a human body. The pulse wave information may be acquired from a body part other than the face, including exposed parts of the body such as the palm and the neck.

Figure 7:
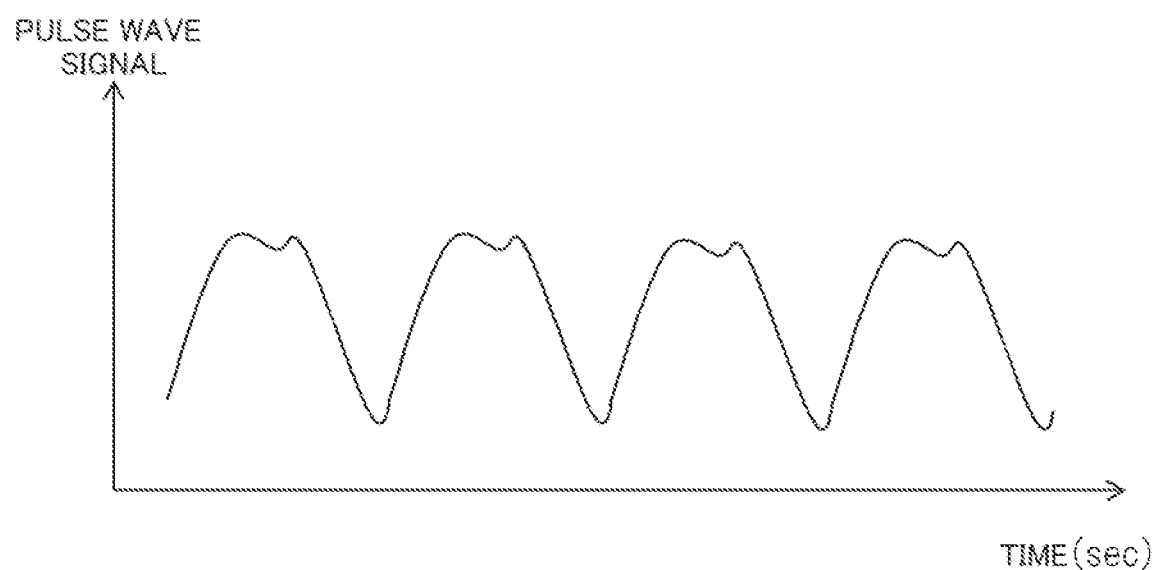
FIG. 7 is a diagram of an exemplary waveform of a pulse wave represented by pulse wave information acquired by a biological information acquisition unit in accordance with an embodiment.

FIG. 7 is a diagram of an exemplary waveform of a pulse wave represented by pulse wave information acquired by the biological information acquisition unit 23 in accordance with an embodiment. The biological information acquisition unit 23 may subsequently acquire various biological information by measuring, for example, the blood pressure, heart rate, stress level, heart rate, or other like information that indicates the physical condition of the blood vessel from the pulse wave represented by the acquired pulse wave information.

Alternatively, the biological information acquisition unit 23 may detect respiration from temporal changes of the luminance value caused by the body movement of the living body captured in the moving image or plurality of successive still images. For instance, the biological information acquisition unit 23 may acquire the body movement of the shoulder or chest that accompanies respiration to acquire the respiration rate, expiration, or inspiration as the biological information.

The pulse wave information and other like biological information acquired by the biological information acquisition unit 23 may be displayed on the display unit 3 or other display device and may be stored in a storage device other than the mobile terminal 1, for example, in a server.

As an example, when the heart rate, stress level, respiration rate, or other like information that can be acquired irrespective of the body part is to be further acquired form the pulse wave represented by the acquired pulse wave information, it is reasonably expected that the precision in detecting information will improve if the target regions A12 and A22 described with reference to FIG. 6 are each specified by identifying a plurality of regions (plurality of body parts) of each person captured in an image and identifying one of these regions (plurality of body parts) that has a high pixel value as the target regions A12 and A22.

As an alternative, the biological information acquisition unit 23 may detect a feature (e.g., nose) in one of the frames of the moving image (or one of the plurality of successive still images) and tracks the coordinates of the detected feature in other frames (or other still images), to specify the target regions A12 and A22 from the tracked coordinates.

As another alternative, the biological information acquisition unit 23 may detect a feature (e.g., nose) in one of the frames (or one of the plurality of successive still images) to specify the target regions A12 and A22 and specify, as the target regions A12 and A22, the same coordinates as the coordinates of the already specified target regions A12 and A22 in other frames (or other still images).

The image capturing unit 6 and the image-capturing control unit 21 in the image capturing device 40 capture a moving image or plurality of successive still images with, for example, a 4K or higher resolution as described here. In other words, the image capturing unit 6 includes a 4K-equivalent number of pixels. The image capturing device 40, if including at least a 4K-equivalent number of pixels, is capable of capturing a moving image or plurality of successive still images with high resolution by using the large number of pixels.

The biological information acquisition unit 23 can hence acquire pulse wave information from the high resolution target regions A12 and A22 captured by a large number of pixels, thereby acquiring high precision pulse wave information.

Since the image capturing device 40 includes at least a 4K-equivalent number of pixels, the image capturing device 40 is capable of capturing a moving image or plurality of successive still images with a high S/N (signal/noise) ratio if, for example, the image capturing device 40 has a pixel size that is equal to the pixel size of the number of pixels that is fewer than 4K. The biological information acquisition unit 23 can hence acquire high precision pulse wave information from the high S/N (signal/noise) ratio, target regions A12 and A22.

The image capturing device 40 is capable of capturing a moving image or plurality of successive still images captured with a high S/N ratio by using a large number of pixels when compared with an image capturing device including fewer than a 4K-equivalent number of pixels even when there is not much ambient light available in capturing a moving image or plurality of successive still images. The biological information acquisition unit 23 can hence acquire high precision pulse wave information from the high S/N ratio, target regions A12 and A22 even when the moving image or plurality of successive still images is captured in a dark environment where there is not much ambient light.

The image capturing device 40 is capable of capturing a moving image or plurality of successive still images with high resolution. Therefore, even when there are two or more people in the image(s), pulse wave information can be precisely acquired for each person in the image(s) from a single shot. The image capturing device 40 can hence efficiently acquire pulse wave information for two or more people.

Furthermore, the mobile terminal 1 is capable of capturing a moving image or plurality of successive still images with high resolution. Therefore, even when the captured image or images show(s) a person at some distance from the image capturing device 40 and with a small size, pulse wave information can be precisely acquired for the person from the image(s). The mobile terminal 1 hence enables acquiring pulse wave information from distance, which adds to convenience.

Figure 8:
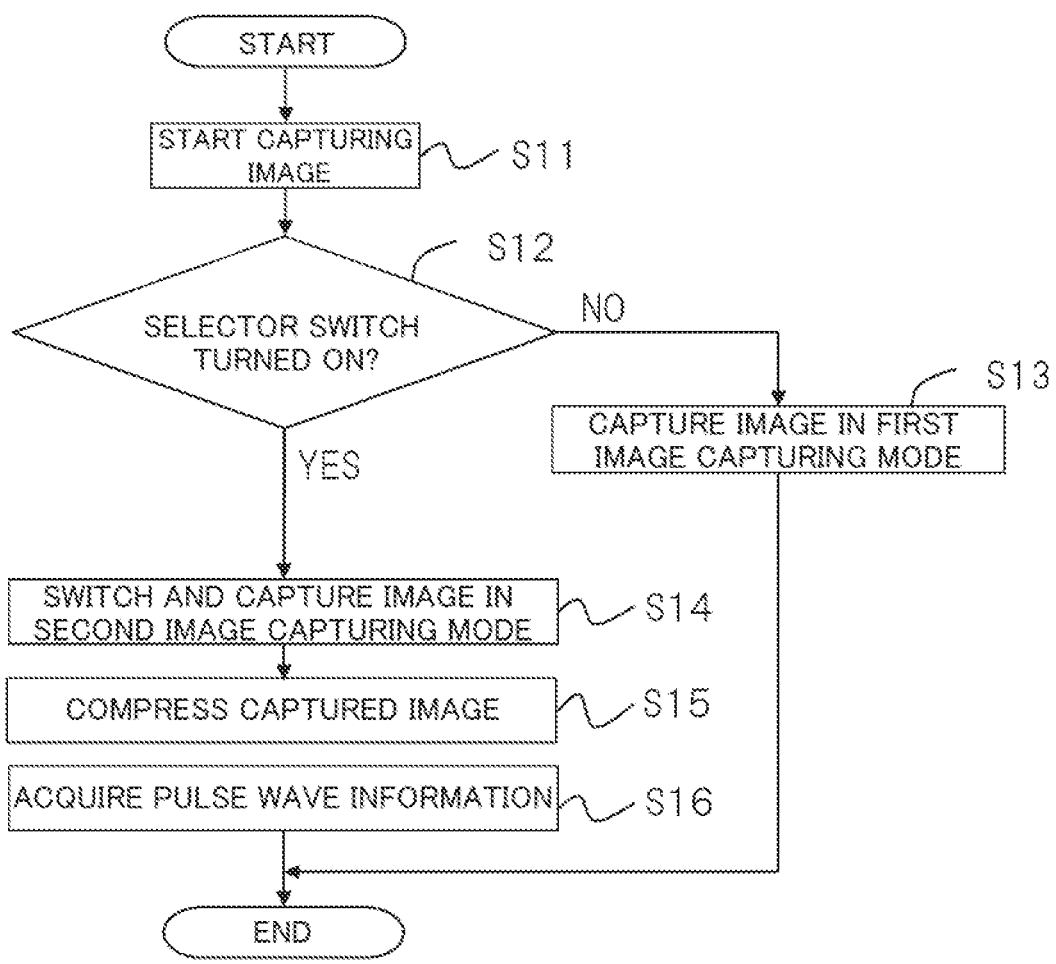
FIG. 8 is a flow chart representing an exemplary operation of a control unit in accordance with an embodiment.

FIG. 8 is a flow chart representing an exemplary operation of the control unit 20 in accordance with an embodiment. Referring to FIG. 8, the image-capturing control unit 21, in step S11, drives the image capturing unit 6 on the basis of an image-capturing command signal that is an input signal coming from the input unit 4 in response to a manual operation by the user to start capturing a moving image or plurality of successive still images.

Then, in step S12, the image-capturing control unit 21 determines whether or not the selector switch 10 has been turned on. Specifically, for example, as long as the image-capturing control unit 21 does not receive from the input unit 4 a switching signal that is an input signal indicating that the selector switch 10 has been turned on, the image-capturing control unit 21 determines that the selector switch 10 is not turned on (NO in step S12) and captures a moving image or plurality of successive still images in the first image capturing mode in step S13. The image-capturing control unit 21 then ends capturing image(s) in the first image capturing mode upon receiving an input signal from the input unit 4 instructing to stop capturing image(s).

Meanwhile, when the image-capturing control unit 21 has received from the input unit 4 a switching signal that is an input signal indicating that the selector switch 10 has been turned on, the image-capturing control unit 21 determines that the selector switch 10 has been turned on (YES in step S12). Then, in step S14, the image-capturing control unit 21 switches to the second image capturing mode and captures a moving image or plurality of successive still images to generate a moving image or plurality of successive still images. Then, the compression unit 22, in step S15, compresses and stores the moving image or plurality of successive still images generated by the image-capturing control unit 21 in the memory unit 30 where necessary.

Next, in step S16, the biological information acquisition unit 23 acquires the moving image or plurality of successive still images stored in the memory unit 30, if the image(s) is/are compressed, decompresses the image(s), and acquires pulse wave information representing a pulse wave from the moving image or plurality of successive still images.

The image-capturing control unit 21 then ends capturing image(s) in the second image capturing mode upon receiving an input signal from the input unit 4 instructing to stop capturing image(s).

The image capturing device 40 includes the image capturing unit 6 and the image-capturing control unit 21 as described above. The image capturing unit 6 and the image-capturing control unit 21 capture a moving image or plurality of successive still images with a 4K or higher resolution. A moving image or plurality of successive still images can be thus captured with a high S/N ratio and high resolution. The image capturing unit 6 and the image-capturing control unit 21 can hence capture a moving image or plurality of successive still images from which high precision pulse wave information can be acquired.

The image capturing device 40 further includes the selector switch 10 for switching the image capturing mode in which the image capturing unit 6 captures a moving image or plurality of successive still images from the first image capturing mode to the second image capturing mode. This particular structure enables the user to, by simply turning on the selector switch 10, switch the image capturing mode for the image capturing device 40 from the first image capturing mode to the second image capturing mode for capturing a moving image or plurality of successive still images with high resolution in detecting the amount of change in pulse wave information representing the pulse wave of a living body captured in the image(s). The image capturing device 40 thus enables switching of the image capturing mode through a simple and convenient operation to settings that are suitable for acquiring pulse wave information, hence improving convenience for the user.

The second image capturing mode captures a moving image or plurality of successive still images using a narrower color gamut than does the first image capturing mode. In other words, as described with reference to, for example, FIG. 3, the image-capturing control unit 21, in the second image capturing mode, uses the second color gamut DIB, which is deliberately narrower than the first color gamut D1A used in the first image capturing mode, in representing the captured moving image or plurality of successive still images. This particular configuration enables capturing a moving image or plurality of successive still images that provides a higher resolution in detecting the amount of change in pulse wave information representing the pulse wave of a living body than in the first image capturing mode. That in turn enables the generation of a moving image or plurality of successive still images from which pulse wave information can be precisely acquired.

The second image capturing mode captures a moving image or plurality of successive still images using a narrower dynamic range than does the first image capturing mode. In other words, as described with reference to, for example, FIG. 4, the image-capturing control unit 21, in the second image capturing mode, uses the second dynamic range D2B, which is deliberately narrower than the first dynamic range D2A used in the first image capturing mode, in representing the captured moving image or plurality of successive still images. This particular configuration enables capturing a moving image or plurality of successive still images that provides a higher resolution in detecting the amount of change in pulse wave information representing the pulse wave of a living body than in the first image capturing mode. That in turn enables the generation of a moving image or plurality of successive still images from which pulse wave information can be precisely acquired.

The mobile terminal 1 includes the image capturing device 40 and the biological information acquisition unit 23. This particular structure enables the biological information acquisition unit 23 to acquire high precision pulse wave information from the moving image or plurality of successive still images captured on the image capturing device 40.

The mobile terminal 1 includes the compression unit 22. The compression unit 22 separately compresses each individual frame in the moving image captured by the image capturing unit 6 and the image-capturing control unit 21 or each individual successive still image captured by the image capturing unit 6 and the image-capturing control unit 21. This particular configuration enables the biological information acquisition unit 23 to acquire high precision pulse wave information from a decompressed moving image or plurality of successive still images.

Figure 9:
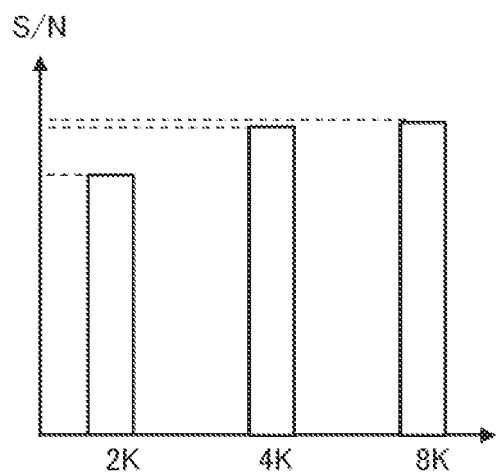
FIG. 9 is a diagram representing a result of comparison of S/N ratios for different pixel resolutions, obtained in Experimental Example 1 in accordance with an embodiment.

FIG. 9 is a diagram representing a result of comparison of S/N ratios for different pixel resolutions, obtained in Experimental Example 1 in accordance with an embodiment. In Experimental Example 1, a camera with an 8K-equivalent number of pixels was used to capture a moving image of a person standing 5 meters from the camera. A 4K-equivalent moving image and a 2K-equivalent moving image were generated by shedding part of an 8K-equivalent moving image. Pulse wave information was acquired from the changes in the color of the faces of people captured in the original 8K-equivalent moving image and the generated 4K-equivalent and 2K-equivalent moving images. An S/N ratio was calculated for each set of pulse wave information.

FIG. 9 shows that the S/N ratio of the pulse wave information acquired from the 4K-equivalent moving image is higher than the S/N ratio of the pulse wave information acquired from the 2K-equivalent moving image and also that the S/N ratio of the pulse wave information acquired from the 8K-equivalent moving image is even higher than the S/N ratio of the pulse wave information acquired from the 4K-equivalent moving image.

Figure 10:
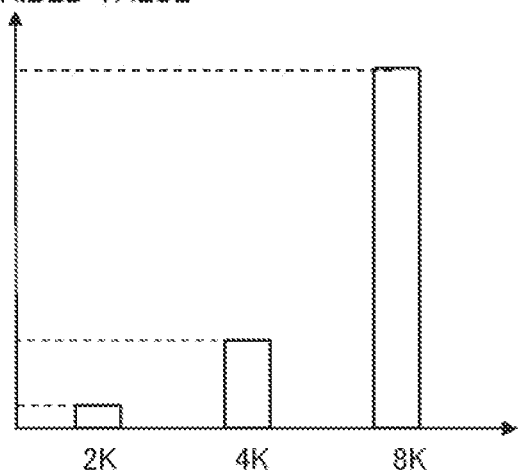
FIG. 10 is a diagram representing a result of comparison of the number of pixels that have a luminance greater than or equal to a prescribed value for different pixel resolutions, obtained in Experimental Example 1 in accordance with an embodiment.

FIG. 10 is a diagram representing a result of comparison of the number of pixels that have a luminance greater than or equal to a prescribed value for different pixel resolutions, obtained in Experimental Example 1 in accordance with an embodiment. Of all the pixels for the face of the person captured in each of the original 8K-equivalent moving image and the generated 4K-equivalent and 2K-equivalent moving images, the number of pixels that have a luminance greater than or equal to a prescribed value was obtained for comparison.

FIG. 10 shows that the 4K-equivalent moving image contains more pixels that have a luminance greater than or equal to a prescribed value than does the 2K-equivalent moving image and also that the 8K-equivalent moving image contains even more pixels that have a luminance greater than or equal to a prescribed value than does the 4K-equivalent moving image.

It is understood that the number of pixels that have a luminance greater than or equal to a prescribed value approximately quadruples in 4K over 2K and approximately further quadruples in 8K over 4K. It is reasonably expected that, for example, the image(s) taken on a 2K resolution camera at the original distance from the subject provides pulse wave information of approximately the same level of precision as the image(s) taken on a 4K resolution camera at double the distance.

Figure 11:
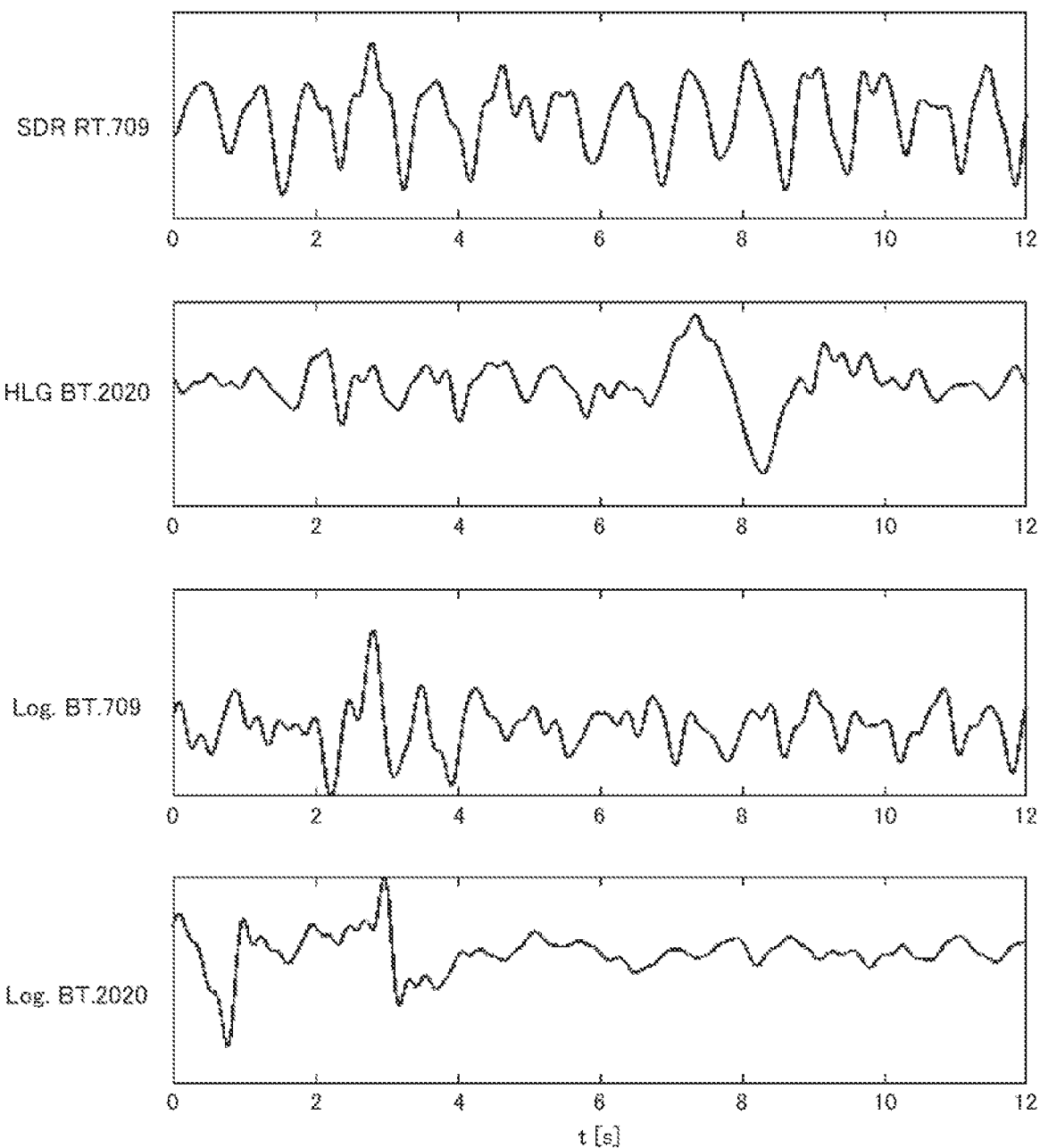
FIG. 11 is a diagram representing a result of comparison of pulse wave information for different parameter settings on a moving image capturing camera, obtained in Experimental Example 2 in accordance with an embodiment.

FIG. 11 is a diagram representing a result of comparison of pulse wave information for different parameter settings on a moving image capturing camera, obtained in Experimental Example 2 in accordance with an embodiment. In Experimental Example 2, a camera with an 8K-equivalent number of pixels was used to capture a moving image of a person standing 50 centimeters from the camera with different parameter settings.

Figure 12:
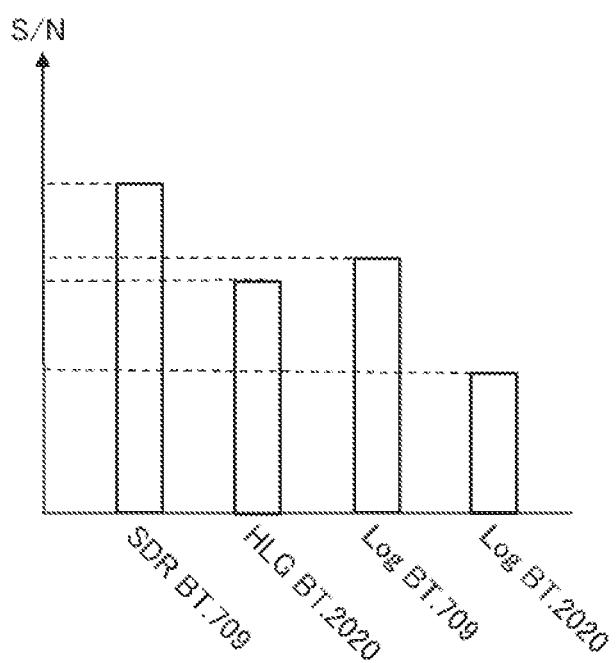
FIG. 12 is a diagram representing a result of comparison of S/N ratios for each parameter in different parameter settings on a moving image capturing camera, obtained in Experimental Example 2 in accordance with an embodiment.

FIG. 12 is a diagram representing a result of comparison of S/N ratios for each parameter in different parameter settings on a moving image capturing camera, obtained in Experimental Example 2 in accordance with an embodiment.

"SDR" (standard dynamic range), "HLG" (hybrid log gamma), and "Log" in FIG. 11 show a dynamic range. "Log gamma" is capable of reproducing small changes in a small range of pixel values (a dark environment). FIG. 11 shows that SDR more precisely represents the waveform of a pulse wave than Log gamma. Comparison of BT. 709 with BT. 2020, both of which represent a color gamut, shows that BT. 2020 more precisely represents the waveform of a pulse wave than BT. 709.

It is understood from FIG. 12 that in Experimental Example 2, the S/N ratio is highest with SDR BT. 709, followed by Log BT. 709 and then by HLG BT. 2020, and is lowest with Log BT. 2020.

Variation Example 1

Figure 13:
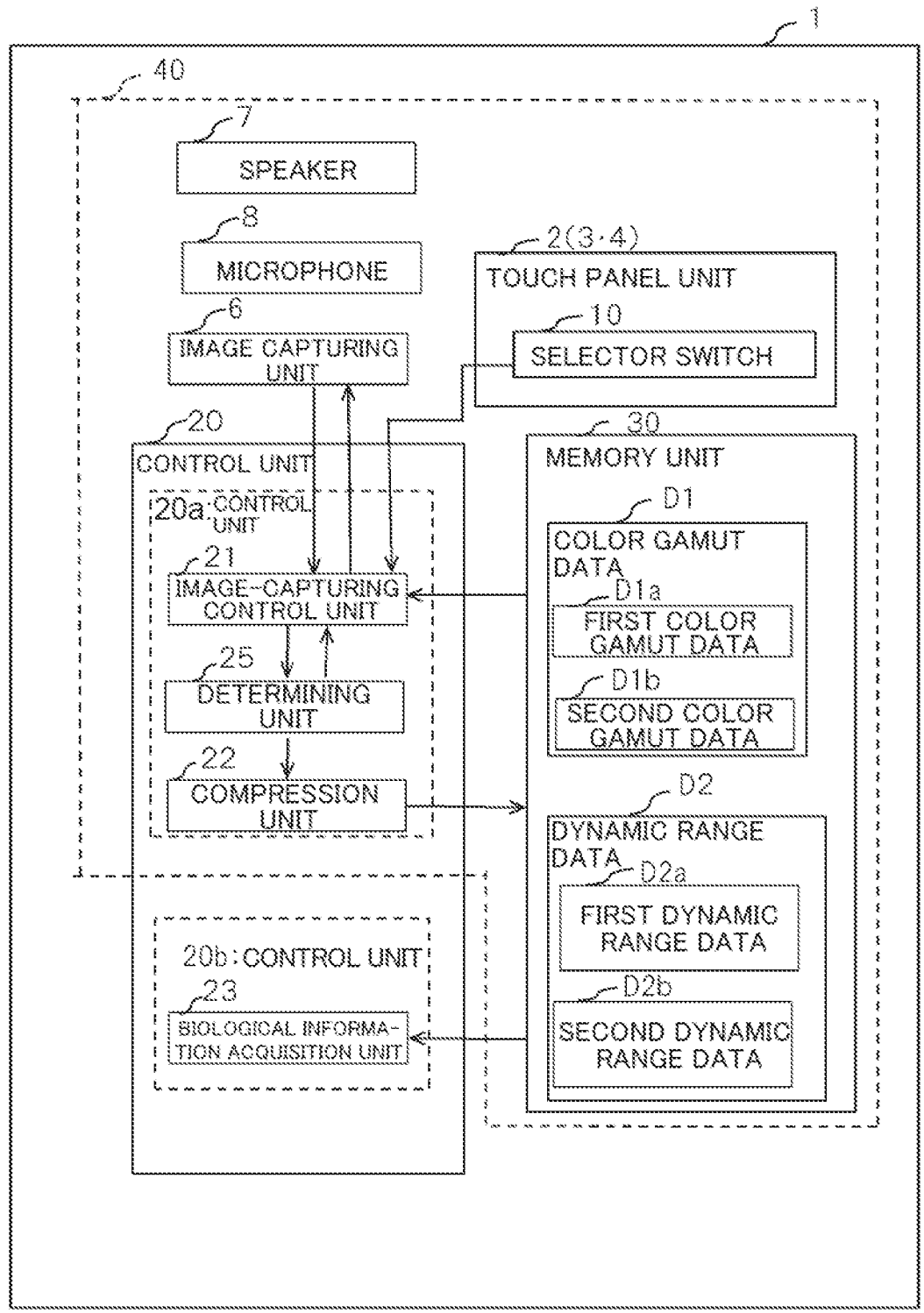
FIG. 13 is a functional block diagram of a mobile terminal in accordance with Variation Example 1 of an embodiment.

FIG. 13 is a functional block diagram of the mobile terminal 1 in accordance with Variation Example 1 of an embodiment. Referring to FIG. 13, the control unit 20 (control unit 20a) of the image capturing device 40 may further include a determining unit 25. FIG. 14 is a flow chart representing an exemplary operation of the control unit 20 in accordance with Variation Example 1 of an embodiment.

Assume that after carrying out step S11 and following "NO" in step S12 in FIG. 14, the image capturing unit 6 and the image-capturing control unit 21 are capturing a moving image or plurality of successive still images in the first image capturing mode.

Next, in step S13A, while the image capturing unit 6 and the image-capturing control unit 21 are capturing a moving image or plurality of successive still images in the first image capturing mode, the determining unit 25 determines whether or not there is a human or other living body in the moving image or plurality of successive still images. Then, upon determining that there is a living body in the moving image or plurality of successive still images captured in the first image capturing mode ("YES" in step S13A), the determining unit 25 instructs the image capturing unit 6 and the image-capturing control unit 21 to switch the image capturing mode from the first image capturing mode to the second image capturing mode. In response to this instruction, the image capturing unit 6 and the image-capturing control unit 21 switch the image capturing mode from the first image capturing mode to the second image capturing mode in capturing a moving image or plurality of successive still images (step S14). The process then proceeds to steps S15 and S16.

As described here, the provision of the determining unit 25 enables the image capturing device 40 to switch from the first image capturing mode to the second image capturing mode in capturing a moving image or plurality of successive still images, without having to wait for the user to turn on the selector switch 10. This particular configuration can further save the user trouble in acquiring pulse wave information. The image capturing device 40 can hence provide a simpler and more convenient process of switching the image capturing mode to settings that are suitable for acquiring pulse wave information.

Variation Example 2

The image capturing device 40 or any other entity for performing an image capturing method in accordance with the present disclosure includes a computer as the control unit 20a. This computer runs an image-capturing program to provide the functions of the image capturing device 40 or the entity for performing the image capturing method in accordance with the present disclosure.

The mobile terminal (information acquisition device) 1 or any other entity for performing an information acquisition method in accordance with the present disclosure includes a computer as the control unit 20. This computer runs an information acquisition program to provide the functions of the mobile terminal (information acquisition device) 1 or the entity for performing the information acquisition method in accordance with the present disclosure.

The computer includes a processor that operates in accordance with the image-capturing program and the information acquisition program as a primary hardware component. The processor may be of any kind so long as the processor is capable of providing functions by running the image-capturing program and the information acquisition program. The processor includes one or more electronic circuits including a semiconductor integrated circuit (IC) or LSI (large scale integration) chip. The electronic circuits may be integrated into a single chip or provided in multiple chips. The chips may be combined into a single device or provided in multiple devices. The image-capturing program and the information acquisition program are stored in a computer-readable, non-transitory recording medium such as a ROM, an optical disc, or a hard disk drive. The image-capturing program and the information acquisition program may be contained in such a recording medium in advance or delivered to the recording medium over an electric telecommunication line such as the Internet.

The present invention is not limited to the description of the embodiments and examples above. Any structure detailed in the embodiments and examples may be replaced by a practically identical structure, a structure that achieves the same effect and function, or a structure that achieves the same purpose.

While there have been described what are at present considered to be certain embodiments of the invention, it will be understood that various modifications may be made thereto, and it is intended that the appended claims cover all such modifications as fall within the true spirit and scope of the invention.

What is claimed is:

1. An image capturing device comprising:
a sensor device configured to capture a moving image having a 4K or higher resolution;
an imaging control unit configured to, in a case that the moving image contains a living body, switch an image capturing mode, in which the sensor device captures the moving image, from a first image capturing mode to a second image capturing mode, the second image capturing mode providing a higher resolution for the captured moving image, than a resolution for the captured moving image provided by the first image capturing mode, in detecting an amount of change in pulse wave information representing a pulse wave of the living body in the captured moving image;
a judgment unit for determining whether or not the living body is reflected in the moving image; and
a biological information acquisition unit configured to acquire the pulse wave information from the moving image captured in the second image capturing mode, wherein
the biometric information acquisition section acquires the pulse wave information by identifying (i) a partial region of the living body, (ii) a plurality of sites from the partial region, and (iii) a site, among the plurality of sites, that has a largest pixel value, as a region of interest, and acquiring the pulse wave information from the region of interest.

2. An image capturing device comprising:
a sensor device configured to capture a moving image, having a 4K or higher resolution; and
a selector switch configured to switch an image capturing mode, in which the sensor device captures the moving image, from a first image capturing mode to a second image capturing mode, the second image capturing mode providing a higher resolution for the captured moving image, than a resolution for the captured moving image provided by the first image capturing mode, in detecting an amount of change in pulse wave information representing a pulse wave of a living body in the captured moving image,
wherein the moving image is generated by using at least one of a narrower color gamut and a narrower dynamic range in the second image capturing mode than in the first image capturing mode.

3. A biological information acquisition device comprising:
the image capturing device according to claim 2; and a biological information acquisition unit configured to acquire the pulse wave information from the moving image captured in the second image capturing mode.

4. The biological information acquisition device according to claim 3, further comprising:
   a determining unit configured to determine whether the moving image shows the living body; and
   an image-capturing control unit configured to, when the moving image shows the living body, switch the image capturing mode from the first image capturing mode to the second image capturing mode for the sensor device.

5. The biological information acquisition device according to claim 1, further comprising a compression unit configured to separately compress each of a plurality of frames contained in the moving image captured by the sensor device.

6. The biological information acquisition device according to claim 3, further comprising a compression unit configured to separately compress each of a plurality of frames contained in the moving image captured by the sensor device.

7. An image capturing method comprising:
   acquiring an input signal;
   in response to acquiring the input signal, switching an image capturing mode of a captured moving image from a first image capturing mode to a second image capturing mode in a case that the captured moving image contains a living body, the second image capturing mode providing a higher resolution for the captured moving image, than a resolution for the captured moving image provided by the first image capturing mode, in detecting an amount of change in pulse wave information representing a pulse wave of the living body in the captured moving image;
   determining whether or not the living body is reflected in the captured moving image; and
   acquiring the pulse wave information from the captured moving image in the second image capturing mode, wherein
   the acquiring of the pulse wave information comprises:
      identifying a partial region of the living body,
      identifying a plurality of sites from the partial region,
      identifying a site, among the plurality of sites, that has a largest pixel value, as a region of interest, and
      acquiring the pulse wave information from the region of interest.

8. The biological information acquisition device according to claim 4, further comprising a compression unit configured to separately compress each of a plurality of frames contained in the moving image captured by the sensor device.

* * * * *